(12) United States Patent
Dauner et al.

(10) Patent No.: US 8,685,649 B2
(45) Date of Patent: Apr. 1, 2014

(54) RT-LAMP ASSAY FOR THE DETECTION OF PAN-SEROTYPE DENGUE VIRUS

(75) Inventors: Allison Dauner, Rockville, MD (US); Subhamoy Pal, Silver Spring, MD (US); Shuenn-Jue Wu, Rockville, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 358 days.

(21) Appl. No.: 13/156,435

(22) Filed: Jun. 9, 2011

(65) Prior Publication Data

US 2011/0306036 A1   Dec. 15, 2011

Related U.S. Application Data

(60) Provisional application No. 61/353,306, filed on Jun. 10, 2010.

(51) Int. Cl.
| | | |
|---|---|---|
| *C12Q 1/68* | (2006.01) | |
| *C12Q 1/70* | (2006.01) | |
| *C07H 21/02* | (2006.01) | |
| *C07H 21/04* | (2006.01) | |

(52) U.S. Cl.
USPC ............. 435/6.12; 435/5; 536/23.1; 536/24.3

(58) Field of Classification Search
None
See application file for complete search history.

(56) References Cited

U.S. PATENT DOCUMENTS

| | | | |
|---|---|---|---|
| 2004/0248325 A1 * | 12/2004 | Bukusoglu | 436/548 |
| 2005/0227275 A1 * | 10/2005 | Jung et al. | 435/6 |
| 2006/0018928 A1 | 1/2006 | Pang | |
| 2006/0062803 A1 | 3/2006 | Kinney et al. | |
| 2007/0009552 A1 | 1/2007 | Whitehead et al. | |
| 2008/0318208 A1 | 12/2008 | Puffer et al. | |
| 2012/0088244 A1 * | 4/2012 | Owen et al. | 435/6.12 |

OTHER PUBLICATIONS

GenBank Accession No. NC_001477 (Jun. 2000).*
GenBank Accession No. NC_001474 (Nov. 2007).*
GenBank Accession No. NC_001475 (Dec. 2007).*
GenBank Accession No. NC_002640 (Jan. 2001).*
Sudiro, T.M. et al., Am. J. Trop. Med. Hyg., vol. 56, pp. 424-429 (1997).*
Iseki, H. et al., J. Microbiol. Meth., vol. 71, pp. 281-287 (2007).*
Yamazaki, W. et al., Appl. Env. Microbiol., vol. 76, pp. 820-828 (Feb. 2010).*
Aonuma, H. et al., Exp. Parasitol., vol. 125, pp. 179-183 (Jan. 2010).*
Primer Explorer, V3 (Mar. 2007); downloaded from web.archive.org/web/20070311134718/http://primerexplorer.jp/e/ Jul. 30, 2013.*
Landgraf, A. et al., Anal. Biochem., vol. 198, pp. 86-91 (1991).*
Poon, L.L.M. et al., Clin. Chem., vol. 52, pp. 303-306 (2006).*
Ihira, M. et al., J. Clin. Virol., vol. 39, pp. 22-26 (2007).*
Parida, et al, Rapid detection and differentiation of dengue virus serotypes by a Real-Time Reverse Transcription-Loop-Mediated Isothermal Amplification Assay, J Clin Microbiol. 2005, 43: 2895-2903.
Yong, et al., Rapid detection and serotyping of dengue virus by multiplex RT-PCR and real-time SYBR green RT-PCR. Singapore Med J. 2007 48: 662-668.
Notomi, et al., Loop-mediated isothermal amplification of DNA. Nucleic Acids Res. 2000 28: E63.
Curtis, et al., Sequence-specific detection method for reverse transcription, loop-mediated isothermal amplification of HIV-1. J Med Virol. 2009: 81: 966-972.
GenBank_BV222814, S233P667RE3.T0 Labrador Retriever *Canis familiaris* STS genomic, sequence tagged site, Jan. 19, 2005 (online). Retreived from Internet: <URL: http://www.ncbi.nlm.nih.gov/nuccore/BV222814>, the sequence comprises a region between nucleotides 328-311 that is 100% identical to that claimed in SEQ ID No. 6.
GenBank_GQ293091, Dengue virus 3 polyprotein gene, partial cds, Aug. 25, 2009 (online). From Internet <URL: http://www.ncbi.nlm.nih.gov/nuccore/GQ293091>. The sequence comprises region between nucleotides 155-172 that is 94.4% identical to SEQ ID No. 6.
GeneBank_EU482608, Dengue virus 2 isolate DENV-2/VE/BID-V1111/2007, complete genome Jun. 2, 2009 (online). From Internet <URL: http://www.ncbi.nlm.nih.gov/nuccore/EU482608>. Sequence is 61.6% identical to SEQ ID No. 3.
GenBank_FJ639748, Dengue virus 4 isolate DENV-4VE/BID-V2177/2000, complete genome Jan. 26, 2009 (online). From internet <URL: http://www.ncbi.nlm.nih.gov/nuccore/FJ639748>. Sequence is 58.8% identical to SEQ ID No. 4.
GenBank_AC015504, *Homo sapiens* clone RP11-21H5, Working Draft Sequence, May 12, 2000 (online). From Internet: URL://www.ncbi.nlm.nih.gov/nuccore/AC015504> Comprises a region between nucleotides 51075-51123 that is 57.6% identical to SEQ ID No. 8.
GenBank_AC117354, *Rattus norvegicus* clone CH230-154L15 from Oct. 9, 2002 (online). From Internet: <URL://www.ncbi.nlm.nih.gov/nuccore/AC117354>. Sequence comprises a region between nucleotides 242819-242771 that is 57.6% identical to SEQ ID No. 9.

* cited by examiner

*Primary Examiner* — Teresa E Strzelecka

(74) *Attorney, Agent, or Firm* — Albert M. Churilla; Ning Yang; Joseph K. Hemby

(57) ABSTRACT

The invention relates to a reverse transcription loop-mediated isothermal amplification (LAMP) assay for the detection of dengue virus. The assay is capable of simultaneous detection of dengue 1-4 serotypes in a single reaction.

10 Claims, 2 Drawing Sheets

RT-LAMP ASSAY FOR THE DETECTION OF PAN-SEROTYPE DENGUE VIRUS

CROSS-REFERENCES TO RELATED APPLICATIONS

This application claims the benefit of U.S. Provisional Application No. 61/353,306, filed Jun. 10, 2010, which is incorporated by reference, herein.

BACKGROUND

1. Field of Invention

The inventive subject matter relates a reverse transcription loop-mediated isothermal amplification (RT-LAMP) assay for detecting pan-serotype dengue virus.

2. Background Art

Dengue virus, the causative agent of dengue fever (DF) and dengue hemorrhagic fever (DHF), is a virus of the genus Flavivirus, a single-stranded enveloped RNA virus with positive polarity. Its RNA encodes approximately 3,400 amino acids. The virus exists as four antigenically-distinguishable serotypes.

Dengue fever is the most common human arbovirus infection worldwide and a serious public health concern accounting for estimates of 100 million infections annually (WHO, *Dengue Hemorrhagic Fever: Diagnosis, Treatment and Control*. Geneva: WHO (1986); Monath and Heinz, Flaviviruses. In Fields Virology. B. N. Fields, D. M. Knipe and P. M. Howley, (eds.) Lippincott-Raven, Philadelphia. 961-1034 (1996); Thomas, et al, Adv. Virus Res. 61: 235-289 (2003). DF and DHF are found in most tropical areas including Africa, Asia, the Pacific, Australia, and the Americas.

Although the virus is capable of growing in a variety of species of mosquitoes, including *Aedes albopictus, Aedes polynesiensis* and *Aedes scutellaris, Aedes aegypti* is the most efficient mosquito vector because of its domestic habitat (Gubler, D. I., Dengue. In *The Arboviruses: Epidemiology and Ecology*. T. P. Monath (ed.), CRC Press (Boca Raton), p 223-260 (1988)). Four antigenically distinct serotypes of dengue virus have been identified with all causing human diseases (Gubler, et al., Am. J. Trop. Med. Hyg. 28:1045-1052 (1979); Henchal and Putnak, Clin. Microbiol. Rev. 3: 376-396 (1990)). Each of the four serotypes, although distinct, is similar enough to the others to elicit only partial cross-protection following infection (WHO, *Dengue Hemorrhagic Fever: Diagnosis, Treatment and Control*. Geneva: WHO (1986); Monath and Heinz, Flaviviruses. In *Fields Virology*. B. N. Fields, D. M. Knipe and P. M. Howley, (eds.) Lippincott-Raven, Philadelphia. 961-1034 (1996)). Following infection, viremia is typically detected early at the onset of symptoms (Halstead, S. B., *Epidemiology of dengue and dengue hemorrhagic fever*. In *Dengue and Dengue Hemorrhagic Fever*. D. J. Gubler and G. Kuno, editors. Cab international, London. 23-44 (1997)). Although many dengue infections are mild, some infections result in DHF and dengue shock syndrome (DSS), which are potentially fatal. This usually occurs in a small number of people during a second infection caused by a dengue virus that is different from the virus causing the first infection (Halstead, S. B., *Epidemiology of dengue and dengue hemorrhagic fever*. In *Dengue and Dengue Hemorrhagic Fever*. D. J. Gubler and G. Kuno, editors. Cab international, London. 23-44 (1997)).

Dengue virus infection occurs following the bite of dengue virus-infected *Aedes* mosquitoes, which were previously infected by feeding on infected humans. Symptoms of dengue infection include high fever, severe headache, retro-orbital pain, development of a rash, nausea, joint and muscle pain, and usually start within five to six days following the bite of an infected mosquito. Symptoms of DHF also include marked sub-dermal bleeding, causing a purplish bruise, as well as bleeding from the nose, gums, and gastrointestinal (GI) tract. The fatality rate associated with DHF is at 6 to 30% with most deaths occurring in infants. The management of DHF is symptomatic and supportive, and is aimed at replacement of fluid loss.

It is not possible to make an accurate diagnosis of mild or classic DF based on clinical features alone since many symptoms of DF resemble those of other diseases, such as Chikungunya infection (Nimmannitya, S., *Dengue and dengue haemorrhagic fever*. In *Manson's Tropical Diseases*. G. C. Cook (eds.) W.B. Saunders Company, Ltd (London). 721-729 (1996)), measles, influenza, and Rickettsial infections. Differential diagnosis must include malaria and other viral, bacterial, and Rickettsial diseases. Diagnostic methods for infection are typically based on detection of virus, viral antigens, genomic sequences, and detection of dengue-specific antibodies (Shu and Huang, Clin. Diagn. Lab. Immunol., 11: 642-650 (2004)). DHF can, in some cases, be more accurately diagnosed based on clinical signs and symptoms, including high continuous fever for 2 to 7 days, hepatomegaly, hemoconcentration, shock and thromocytopenia.

SUMMARY OF THE INVENTION

The most common molecularly-based technique currently used for dengue virus detection is reverse transcription polymerase chain reaction (RT-PCR). Although the method is sensitive, it has inherent disadvantages, including the relatively high skill level required to perform the procedure, expense of the equipment necessary and requirement for multiple temperature cycles, which can complicate establishing efficient procedures.

A preferred embodiment is a reverse transcription loop-mediated isothermal amplification (RT-LAMP) assay method. The embodied method includes primers enabling detection RNA of dengue virus serotypes 1, 2, 3 and 4, simultaneously. The inventive assay provides for rapid and inexpensive detection or diagnosis of dengue virus infections.

In a preferred embodiment, an early step in the inventive assay method comprises converting dengue RNA into DNA through reverse transcription. Subsequently, primer specific amplification of large, detectable quantities of nucleic acid is conducted with final detection of the amplified products. Detection of amplified products is contemplated to be carried out by any of a number of methods, including sequence specific detection using a fluor-labeled probe specific to the LAMP-created DNA loops and DNA fluorescence under UV light using DNA dyes.

DETAILED DESCRIPTION OF PREFERRED EMBODIMENTS

Figure 1:
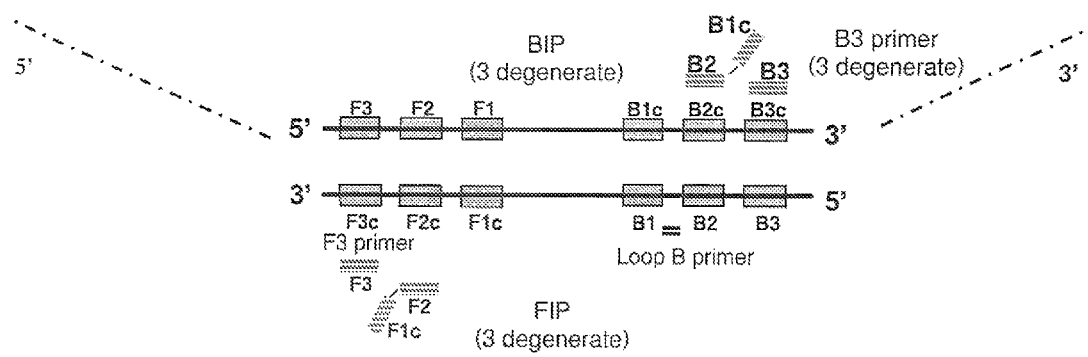
FIG. 1. Diagrammatic illustrating alignment of dengue serotypes and configuration of LAMP primers.

The most common technique currently used to detect dengue virus RNA is Reverse Transcription-Polymerase Chain Reaction (RT-PCR) (McAvin. et at Mil Med., 170: 1053-1059 (2005)). There are currently no FD approved RT-PCR assays for the diagnosis of dengue. However, there are significant disadvantages to using RT-PCR. These include the relatively high skill level required to perform the procedure, expense of the equipment necessary and requirement for multiple temperature cycles, which can complicate establishing efficient procedures.

Therefore, other approaches are desired for detection or diagnosis of dengue virus or dengue fever. The RT-LAMP technique offers advantages over PCR in that the LAMP procedure can be run at one steady temperature, versus the need for a thermocycling equipment when using PCR (Notomi, et al., Nucleic Acids Res, 28:e63 (2000)). Consequently, LAMP assays offer greater speed in obtaining results and less susceptibility to inhibitory substances (Kaneko, et al., J. Biochem., Biophys. Methods, 70: 499-501 (2007)), such as those present in whole blood, serum or target matrix.

In a preferred embodiment, the inventive method comprises the use of primers, which recognize all four dengue serotypes. Therefore, in a single RT-LAMP amplification, all four dengue serotypes can be simultaneously detected in a single reaction tube. Furthermore, detection can be achieved using a number of technologies, ranging from simple illumination of the reaction tube with UV light or, if real-time analysis is desired, detection can be by spectrophotometry.

The inventive primers are summarized in Table 1, which include inner and outer primers sets. The outer sets specifically recognize dengue virus and are designated "ID1:F3"; "B3"; "B3 degen ⅓" or "B3 degen 4." These outer primers, collectively, recognize all four dengue serotypes. The inner primers include: "ID1:BIP degen ⅓", which recognizes nucleic acid sequences from dengue 1 and 3; "ID1:BIP", which recognizes dengue 2; and the primer "ID1:BIP degen 4", which recognizes dengue 4.

TABLE 1

Primer sequences

| Primer | Sequence | SEQ ID No. |
|---|---|---|
| ID1 F3 | gtg gac cga caa aga cag | 1 |
| ID1 FIP | ggt tat tca tca gag atc tgc tct ctt tta ttc ttt gag gga gct aag c | 2 |
| ID 1 FIP degen 1/3 | ggt tat tca tca gag atc tgc tct ctt ttt ttc gaa tcg gaa gct tgc t | 3 |
| ID1 FIP degen 4 | ttc att ttt cca gag atc tgc tct ctt ttt ttc gaa tcg gaa gct tgc t | 4 |
| ID1 B3 | tgc agc att cca agt gag | 5 |
| ID1 B3 degen 1/3 | gtc agc aat cct ttt gag | 6 |
| ID1 B3 degen 4 | gaa aaa agt ccg gtt gag | 7 |
| ID1 BIP | aac gga aaa agg cga gaa ata cgc ttt tct ttg tca gct gtt gca cag t | 8 |
| ID1 BIP degen 1/3 | aac gga aaa aga cgg gtc aac cgt ttt tct tcg cca act gtg aac cag t | 9 |
| ID1 BIP degen 4 | aac gaa aaa agg tgg tta gac cac ttt tct tca cca acc ctt gag ggg t | 10 |
| ID1 + 6 LoopB | gcg aga gaa acc gcg tgt c | 11 |
| FAM-ID1 + 6LoopB | cgc gag aga aac cgc gtg tc | 12 |
| BHQ-LoopBRevComp | gac acg cgg ttt ctc tcg cg/3BHQ_1 | 13 |

Also, the results can often by determined as positive or negative using a UV fluorescent light or even the naked eye.

RT-LAMP assays for the detection of dengue virus has been developed and described in the literature by Parida, et al (J. Clin. Microbiol. 43(6): 2895-903 (2005)). However, the Parida, et al. assay requires running four separate reactions to detect the 4 distinct serotypes of dengue virus. Because four assays are needed, there is a concomitant increase in time, cost and complexity of assay design and operation.

An embodiment of the current inventive assay is a method incorporating primers to unique and conserved regions of the dengue genome. This enables detection of all four serotypes, simultaneously. This feature, therefore, significantly increases the value of RT-LAMP in dengue diagnosis.

FIG. 1 illustrates the functional relationship of the primers. The regions illustrated are present in all primers specific to each dengue strain. F3 is used to create a double stranded DNA template. The inner FIP primers each contain two regions, an F2 and F1c region. Similarly, for BIP-initiated primers contain a B2 and B1c region. The LAMP reaction is initiated, subsequent to creation of a double-stranded DNA template, when the F2 region of the FIP inner primers, binds to the F2c region of one strand of the DNA template and initiates DNA strand extension. The F3 primer then anneals to the F3c region, 5' to the F2 region, which initiates displacement of and release of the FIP-linked complementary strand.

Subsequently, F1c binds to the complementary sequence in F1 forming a loop structure. The LoopB primers recognize the loop regions formed during the LAMP process. A similar sequence of events occurs with the BIP primers at the opposite end of the DNA template. The end result is a DNA structure with stem-loops at opposite ends. This structure is then amplified. It is this amplified structure that is ultimately detected as a positive indication of dengue.

The specificity of the inventive method is incorporated and resulting from several aspects inherent in the inventive method, including: 1) the specificity of the outer primers, i.e., F3 and B3, for dengue virus; 2) from the degenerate primers, which are dengue serotype specific; and 3) in the notion that the degenerate primers must bind to both strands of DNA but in different regions. For example, in F2-F1c, F2 must bind to one strand and F1c must bind to a different region complementary region of the same strand. Additional specificity is provided by the LoopB primers.

A "master mix" is typically formulated to contain all necessary primers and reagents to detect all four dengue serotypes. An example of a "master mix" formulation is illustrated in Table 2. The 10× reaction buffer shown in Table 2 buffer can include a number of formulations. However, in a preferred embodiment, the mix comprises: 200 mM Tris-HCl; 100 mM $(NH_4)_2SO_4$; 100 mM KCl; 20 mM Mg $SO_4$; 0.1% Triton X-100 at pH 8.8 at 25° C. An example of a formulation is ThermoPol Buffer™ (New England Biolabs, Ipswich, Mass.).

TABLE 2

Master Mix

| Reagent | Volume (μL) | Final Concentration |
|---|---|---|
| ID1: FIP | 0.2 | 20 pmol |
| ID1: FIP degen 1/3 | 0.3 | 30 pmol |
| ID1: FIP degen 4 | 0.2 | 20 pmol |
| ID: BIP | 0.2 | 20 pmol |
| ID: BIP degen 1/3 | 0.3 | 30 pmol |
| ID1: BIP degen 4 | 0.2 | 20 pmol |
| ID1: F3 | 0.25 | 2.5 pmol |
| ID1: B3 | 0.25 | 2.5 pmol |
| ID1: B3 degen 1/3 | 0.25 | 2.5 pmol |
| ID1: B3 degen 4 | 0.25 | 2.5 pmol |
| ID1 + 6: LoopB[1] | 0.3 | 30 pmol |
| 10X Reaction Buffer containing: | 2.5 | 1X |
| Betaine | 2 | 0.4M |
| dNTP (dTTP; dATP; dGTP; dCTP) | 3.5 | 1.4 mM each |
| $MgSO_4$ | 0.15 | 8 mM total (w/1X Reaction Buffer) |
| Bst Polymerase | 2 | 16 U |
| AMV-Reverse Transcriptase | 0.16 | 2.4 U |
| Water | 7.99 | |
| Nucleic acid stain[2] | 1 | 0.4X (SYBRSafe) |

[1]Substitute with FAM-LoopB if detection is to be by sequence-specific detection fluorescence followed by quenching.
[2]Required for real-time detection of non-specific DNA amplification. Otherwise substitute with water and visualize ensuing product via agarose gel electrophoresis or post-amplification addition of gel-staining dye followed by UV exposure..

Detection of the LAMP amplified products is via a number of methods. In a preferred embodiment, detection of product is conducted by including a fluorescently-labeled probe to the primer mix. If detection is to be by fluorescence, a fluor, such as 56-FAM, is inserted at the 5' end of the LoopB probe. For example, referring to Table 1, FAM-ID1+6LoopB is shown (SEQ ID No. 12) is included in the master mix, in place of ID1+LoopB (SEQ ID No. 11). At the termination of the reaction, a primer, comprised of the reverse complement of LoopB coupled to a quencher (SEQ ID No. 13), is added. The quencher is added to control for unbound fluor. In an embodiment, fluorescein (FAM) is used in conjunction with Blackhole Quencher™ (BHQ™)(Novato, Calif.). BHQ™ is typically added one hour after beginning the amplification reaction. Binding of the probe to amplified product can then be directly, visually assessed. Alternatively, the fluorescence level can be measured by spectroscopy in order to improve sensitivity.

EXAMPLE 1

Lamp Analysis of Dengue Nucleic Acid and Visualization by Agarose Gel or UV Light As an illustration of the inventive method, wherein detection is by sequence-specific detection by fluorescence, the assay comprises the following steps:
  a. Adding to a tube, 22 μL of the "master mix", containing oligonucleotides SEQ ID No. 1-10, containing primers for dengue 1, 2, 3 and 4, and SEQ ID No. 12. In a preferred embodiment, the master mix comprises those components shown in Table 2.
  b. Add 3 μl of water (control) or RNA to the tube in (a);
  c. Heat tubes at 63° C. for 60 minutes;
  d. Adding 0.6 μL of SEQ ID No. 13 (BHQ™ conjugated LoopB reverse complement primer (LoopBRevComp)) and incubate for approximately 1 hour;
  e. Detecting amplified products.

After an appropriate incubation period, typically 1 hour at room temperature when using BHQ-LoopBRevComp, the resulting fluorescence is then measured. The presence of fluorescence is observed using any device capable of detecting the fluor, such as by spectroscopy or a real-time PCR system.

In another embodiment, following RT-LAMP amplification, detection is by separation of the products by agarose gel electrophoresis. Visualization of a positive response, by visualization of DNA fluorescence under UV light, is by either prior inclusion of nucleic acid stain with the primers during the LAMP procedure, if real-time detection is desired, or inclusion of the stain after assay completion. Alternatively, DNA stain can be added following loading of the samples onto the agarose gel. A DNA ladder-like pattern, resulting from multimeric loop structures is evidence of the presence of dengue in the samples. A lack of a ladder-like pattern indicates a negative reaction. Detection by other mechanical means can be utilized to obtain a real-time assessment of DNA amplification. In this embodiment a DNA stain, such as SYBRSafe™ (Life Technologies, Carlsbad, Calif.), is included in the master mix. The ensuing amplified products are then analyzed via spectroscopy.

Figure 2:
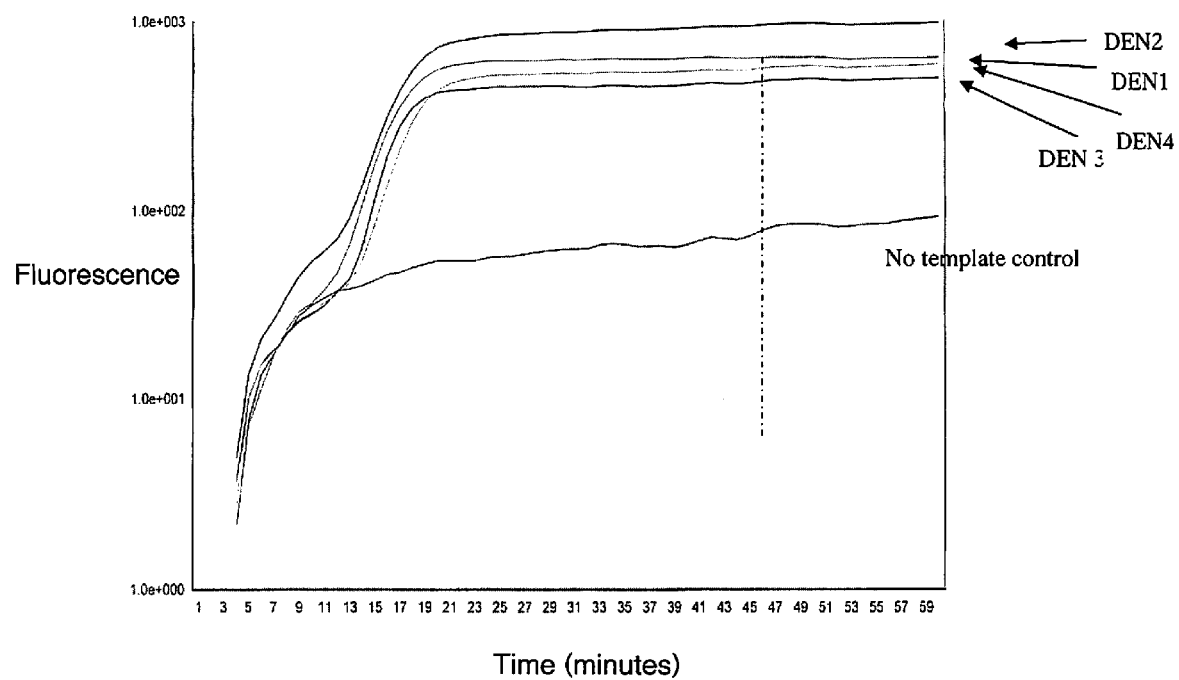
FIG. 2. Detection of four dengue serotypes by real-time RT-LAMP assay using a single set of degenerate primers utilizing real-time monitoring of DNA amplification using SYBRSafe™ fluorescence.

As an illustration, approximately $10^6$ copies of in vitro cultured dengue 1, 2, 3 or 4 were amplified at 63 degrees for 60 minutes. The ensuing products were then analyzed, real-time, on an ABI PRISM® 7000 Sequence Detection System (Life Technologies, Corp, Carlsbad, Calif.). The results of this study are illustrated in FIG. 2, using a single set of degenerate primers via monitoring of DNA amplification using SYBRSafe™ In another embodiment, detection of amplified products can be separated on an agarose gel or, alternatively, the products, can be illuminated, still in the reaction tube, under ultraviolet light after the addition of a DNA stain. Under exposure to UV light, positive samples will yield a fluorescent yellow tint (with SYBRSafe™) and negatives samples will display an orange tint.

The limits of detection were assessed by RT-LAMP, using the above inventive procedure. The results using RT-LAMP were compared with that obtained using RT-PCR and are illustrated in Table 3. As shown in Table 3, the RT-LAMP assay was able to detect down to at least 10 copies, which is equivalent to RT-PCR.

TABLE 3

| Estimated copies/reaction | DEN 1 | | DEN 3 | |
|---|---|---|---|---|
| | RT-LAMP | RT-PCR | RT-LAMP | RT-PCR |
| $10^6$ | + | + | + | + |
| $10^5$ | + | + | + | + |
| $10^4$ | + | + | + | + |
| $10^3$ | + | + | + | + |
| $10^2$ | + | + | + | + |
| 10 | + | ND | + | + |

In this study, samples of dengue 3 were prepared by 1:10 limiting dilution. The sample dilutions were then analyzed with RT-LAMP and RT-PCR. The RT-LAMP procedure is as outlined above, using FAM-LoopB primer (i.e., SEQ ID No. 12). The RT-LAMP tubes were heated to 63° C. for 60 minutes. After addition of BHQ-LoopBRevComp (SEQ ID No. 13) and an appropriate incubation period, typically 1 hour at room temperature, the final fluorescence was measured. Subsequent to amplification, analysis of the RT-LAMP products was via agarose gel electrophoresis and by visual inspection of reaction tubes under UV light. RT-PCR results were analyzed by real-time PCR machine (ABI PRISM® 7000™ Sequence Detection System (Life Technologies, Corp, Carlsbad, Calif.) and agarose gel electrophoresis.

The amount of time necessary to obtain the RT-LAMP result, illustrated in Table 3, was approximately half of that necessary for the results via RT-PCR. Furthermore, the investment in equipment necessary for detection was considerably less for RT-LAMP, compared to RT-PCR, since no thermocycling was needed. In this study, detection of RT-LAMP product was by visual inspection of the product, with a FAM-labeled probe in the reaction tubes under UV light.

Assessment of the RT-LAMP assay with clinical samples indicated a high sensitivity and specificity. In this study, clinical samples, previously characterized as dengue positive by virus isolation and real-time PCR, were used to test the utility of our RT-LAMP assay during natural infection. Normal Human Sera from non-endemic regions were used to assess specificity. Samples were tested in duplicate, and equivocal results were tested in quintuplicate. Using the RT-LAMP assay, 38/44 samples were positive, giving an 86% sensitivity (78.5% to 88.5% at a 95% confidence interval) and 94% specificity (73.8% to 99.7% at a 95% confidence interval).

EXAMPLE 2

Visualization of Lamp Product by Immunochromatographic Assay

In another embodiment, detection of dengue using the inventive LAMP method can be by capturing and visualizing LAMP product on nitrocellulose strips, or similar matrix, by an immunochromatographic assay.

In this embodiment, streptavidin is streaked approximately 3 cm down from one end, containing a sample pad, of a nitrocellulose, or similar matrix, strip. The LAMP assay is conducted as in Example 1. However, for immunochromatographic visualization, the Master Mix (Table 2) also includes 2.5 µl each of 100 µM biotin-11-dUTP and 2.5 µl of 100 µM FITC-12-dUTP. After LAMP reaction, a small sample, typically 2 µl of multiple dilutions of LAMP assay reaction product is spotted onto a sample pad, located on one end of the immunochromatographic matrix strip. As the LAMP products migrate, by capillary effect, down the strip, specifically amplified product is captured by the streptavidin streaked onto the matrix. Development of a purple color after a specified period, typically approximately 30 minutes, equates to a positive reaction. The limits of detection of product via immunochromatographic assay was shown to be similar to that using agarose gel.

What is claimed is:

1. A method of detecting dengue virus in samples containing dengue RNA by LAMP wherein dengue serotypes 1, 2, 3, and 4 are simultaneously detected in a single reaction tube comprising:

a. Adding said samples to a reaction tube;

b. adding to said reaction tube, LAMP reagents, and outside primers specific for dengue virus; degenerate primers specific for dengue serotypes 1, 2, 3 and 4; and a primer specific for LAMP created loop;

c. incubating said reaction tube containing said reagents and primers;

d. detecting LAMP-amplified products, wherein said degenerate primers for said serotypes 1, 2, 3 and 4 contain nucleic acid sequences of SEQ ID No. 2 and SEQ ID No. 8, for serotype 2; SEQ ID No. 3 and SEQ ID No. 9, for serotype 1 and 3; and SEQ ID No. 4 and SEQ ID No. 10, for serotype 4 and wherein said outside primers contain nucleic sequences of SEQ ID No. 1; SEQ ID No. 5; SEQ ID No. 6 and SEQ ID No. 7.

2. The method of claim 1, wherein said primer specific for LAMP created loop is SEQ ID No. 11.

3. The method of claim 1, wherein said detection is by agarose gel electrophoresis.

4. The method of claim 1, wherein biotin-11-dUTP and FITC-12-dUTP is also added to said reaction tube and wherein said detection is by immunochromatographic assay.

5. The method of claim 1, wherein said sample is a clinical sample.

6. The method of claim 1, wherein primer specific for LAMP created loop is conjugated to a fluor on its 5' end and wherein after incubating said reaction tube a LoopB reverse complement primer conjugated to quencher is added followed by a further incubation.

7. The method of claim 5, wherein said clinical sample is whole blood, serum or plasma.

8. The method of claim 6, wherein said primer specific LAMP created loop is SEQ ID No. 12 and said LoopB reverse complement primer is SEQ ID No. 13.

9. The method of claim 6, wherein said fluor is fluorescein.

10. The method of claim 6, wherein said quencher is BHQ.

* * * * *

SEQUENCE LISTING

<160> NUMBER OF SEQ ID NOS: 17

<210> SEQ ID NO 1
<211> LENGTH: 18
<212> TYPE: DNA
<213> ORGANISM: Dengue virus

<400> SEQUENCE: 1
gtggaccgac aaagacag                                          18

<210> SEQ ID NO 2
<211> LENGTH: 49
<212> TYPE: DNA
<213> ORGANISM: Dengue virus

<400> SEQUENCE: 2
ggttattcat cagagatctg ctctctttta ttctttgagg gagctaagc         49

<210> SEQ ID NO 3
<211> LENGTH: 49
<212> TYPE: DNA
<213> ORGANISM: Dengue virus

<400> SEQUENCE: 3

```
ggttattcat cagagatctg ctctcttttt ttcgaatcgg aagcttgct          49

<210> SEQ ID NO 4
<211> LENGTH: 49
<212> TYPE: DNA
<213> ORGANISM: dengue virus

<400> SEQUENCE: 4 ttcattttc cagagatctg ctctcttttt ttcgaatcgg aagcttgct           49

<210> SEQ ID NO 5
<211> LENGTH: 18
<212> TYPE: DNA
<213> ORGANISM: Dengue virus

<400> SEQUENCE: 5
tgcagcattc caagtgag                                            18

<210> SEQ ID NO 6
<211> LENGTH: 18
<212> TYPE: DNA
<213> ORGANISM: Dengue virus

<400> SEQUENCE: 6
gtcagcaatc cttttgag                                            18

<210> SEQ ID NO 7
<211> LENGTH: 18
<212> TYPE: DNA
<213> ORGANISM: Dengue virus

<400> SEQUENCE: 7
gaaaaaagtc cggttgag                                            18

<210> SEQ ID NO 8
<211> LENGTH: 49
<212> TYPE: DNA
<213> ORGANISM: Dengue virus

<400> SEQUENCE: 8
aacggaaaaa ggcgagaaat acgcttttct ttgtcagctg ttgcacagt          49

<210> SEQ ID NO 9
<211> LENGTH: 49
<212> TYPE: DNA
<213> ORGANISM: Dengue virus

<400> SEQUENCE: 9
aacggaaaaa gacgggtcaa ccgttttcct tcgccaactg tgaaccagt          49

<210> SEQ ID NO 10
<211> LENGTH: 49
<212> TYPE: DNA
<213> ORGANISM: Dengue virus

<400> SEQUENCE: 10
aacgaaaaaa ggtggttaga ccacttttct tcaccaaccc ttgaggggt          49

<210> SEQ ID NO 11
<211> LENGTH: 19
<212> TYPE: DNA
<213> ORGANISM: Dengue virus

<400> SEQUENCE: 11
```

```
gcgagagaaa ccgcgtgtc                                                   19
```

<210> SEQ ID NO 12
<211> LENGTH: 20
<212> TYPE: DNA
<213> ORGANISM: Dengue virus

<400> SEQUENCE: 12

```
cgcgagagaa accgcgtgtc                                                  20
```

<210> SEQ ID NO 13
<211> LENGTH: 20
<212> TYPE: DNA
<213> ORGANISM: Dengue virus

<400> SEQUENCE: 13

```
gacacgcggt ttctctcgcg                                                  20
```

<210> SEQ ID NO 14
<211> LENGTH: 120
<212> TYPE: DNA
<213> ORGANISM: Dengue virus

<400> SEQUENCE: 14

```
agttgttagt ctacgtggac cgacaagaac agtttcgaat cggaagcttg cttaacgtag      60
ttctaacagt ttttattag agagcagatc tctgatgaac aaccaacgga aaaagacggg      120
```

<210> SEQ ID NO 15
<211> LENGTH: 120
<212> TYPE: DNA
<213> ORGANISM: Dengue virus

<400> SEQUENCE: 15

```
agttgttagt ctacgtggac cgacaaagac agattctttg agggagctaa gctcaacgta      60
gttctaacag ttttttaatt agagagcaga tctctgatga ataaccaacg aaaaaaggcg      120
```

<210> SEQ ID NO 16
<211> LENGTH: 118
<212> TYPE: DNA
<213> ORGANISM: Dengue virus

<400> SEQUENCE: 16

```
agttgttagt ctacgtggac cgacaagaac agtttcgact cggaagcttg cttaacgtag      60
tgctgacagt ttttattag agagcagatc tctgatgaac aaccaacgga aaagacgg       118
```

<210> SEQ ID NO 17
<211> LENGTH: 124
<212> TYPE: DNA
<213> ORGANISM: Dengue virus

<400> SEQUENCE: 17

```
agttgttagt ctgtgtggac cgacaaggac agttctaaat cggaagcttg cttaacgcag      60
ttctaacagt ttgtttagat agagagcaga tctctggaaa aatgaaccaa cgaaaaaggg      120
tggt                                                                  124
```